US009415078B2

(12) United States Patent
Khamar et al.

(10) Patent No.: US 9,415,078 B2
(45) Date of Patent: Aug. 16, 2016

(54) **METHOD OF TREATING DESMOCOLLIN-3 EXPRESSING CANCER WITH *MYCOBACTERIUM W***

(71) Applicant: Cadila Pharmaceuticals, Ltd., Ahmedabad (IN)

(72) Inventors: Bakulesh Mafatlal Khamar, Ahmedabad (IN); Indravadan Ambalal Modi, Ahmedabad (IN)

(73) Assignee: Cadila Pharmaceuticals Ltd., Ahmedabad (IN)

( * ) Notice: Subject to any disclaimer, the term of this patent is extended or adjusted under 35 U.S.C. 154(b) by 0 days.

(21) Appl. No.: 14/628,534

(22) Filed: Feb. 23, 2015

(65) Prior Publication Data
US 2015/0290255 A1    Oct. 15, 2015

Related U.S. Application Data

(62) Division of application No. 13/978,923, filed as application No. PCT/IB2012/050120 on Jan. 10, 2012, now abandoned.

(30) Foreign Application Priority Data

Jan. 11, 2011  (IN) .............................. 92/MUM/2011

(51) Int. Cl.
*A61K 35/74* (2015.01)
*A61K 45/06* (2006.01)
*C12N 1/20* (2006.01)
A61K 39/04 (2006.01)
A61K 39/00 (2006.01)

(52) U.S. Cl.
CPC ................ *A61K 35/74* (2013.01); *A61K 45/06* (2013.01); *C12N 1/20* (2013.01); *A61K 39/04* (2013.01); *A61K 2039/521* (2013.01); *A61K 2039/585* (2013.01)

(58) Field of Classification Search
None
See application file for complete search history.

(56) References Cited

U.S. PATENT DOCUMENTS

| 7,972,609 | B2 | 7/2011 | Khamar | |
| 2007/0259005 | A1* | 11/2007 | Khamar | A61K 35/74 424/248.1 |
| 2010/0086911 | A1 | 4/2010 | Katsuyama et al. | |
| 2010/0104536 | A1* | 4/2010 | Modi | A61K 35/74 424/93.4 |
| 2012/0328574 | A1 | 12/2012 | Modi et al. | |
| 2013/0295648 | A1* | 11/2013 | Khamar | C12N 1/20 435/253.1 |
| 2014/0294896 | A1* | 10/2014 | Modi | A61K 39/0011 424/277.1 |

OTHER PUBLICATIONS

Sur P. et al. Role of *Mycobacterium w* as Adjuvant Treatment of Lung Cancer. J Indian Med Assoc 101(2)118, 120. Feb. 2003.*
Monica V. et al. Desmocollin-3: A New Marker of Squamous Differentiation in Undifferentiated Large Cell Carcinoma of the Lung. Modern Pathology 22:709-717, 2009.*
International Search Report (4 pgs), dated Mar. 23, 2012 from parent international patent application No. PCT/IB2012/050120, filed on Jan. 10, 2012, which claims priority to and benefit of 92/MUM/2011, filed on Jan. 11, 2011.
Sur P. et al. Role of M. w as Adjuvant Treatment of Lung Cancer. J Indian Med Assoc 101(2)118, 120, Feb. 2003.
Gupta A. et al. Immunogenicity and Protective Efficacy of M. w Against *M tuberculosis* . . . Infection and Immunity 77(1) 223-231, Jan. 2009.
Winter H. et al. Active Specific Immunotherapy for Non-Small Cell Lung Cancer. J of Thoracic Disease 3:105-114, Sep. 2011.

* cited by examiner

*Primary Examiner* — Ralph Gitomer
(74) *Attorney, Agent, or Firm* — Burns & Levinson LLP; Shahid Hasan

(57) ABSTRACT

The present invention relates to increase in survival of mammals suffering from desmocollin 3 expressing cancers. *Mycobacterium w* is administered to mammals suffering from desmocollin-3 expressing cancers. The administration of *Mycobacterium w* results in control of tumor and improvement in survival. *Mycobacterium w* can also be used along with other therapeutic agent(s)/modalities as per the requirement. The squamous type of non small cell lung cancer is known to be desmocollin-3 expressing cancer. Other cancers also express desmocollin-3.

7 Claims, 6 Drawing Sheets

METHOD OF TREATING DESMOCOLLIN-3 EXPRESSING CANCER WITH *MYCOBACTERIUM W*

CROSS REFERENCE TO RELATED APPLICATION

This application is a divisional of U.S. application Ser. No. 13/978,923, filed on Jul. 10, 2013, now abandoned which is a is a §371 U.S. National Stage of PCT Application No. PCT/IB2012/050120, filed Jan. 10, 2012, which was published in English under PCT Article 21(2), which in turn claims the benefit of and priority to the Indian Application No. 92/MUM/2011, filed on Jan. 11, 2011, the entire content of each of which is incorporated herein by reference.

FIELD OF INVENTION

The present invention relates to improving outcome of current therapies for Non Small cell Lung Cancer, particularly that of Squamous cell carcinoma of the lung. The present invention further relates to providing a novel therapy for tumors expressing desmocollin-3.

BACKGROUND OF INVENTION

Lung cancer is the leading cause of cancer-related Deaths world wide with 1.2 million new cases diagnosed every year and with 1 million deaths being recorded worldwide in 2001. Lung cancer is divided into two main groups, small cell lung cancer and non-small cell lung cancer. Approximately 75%-85% of these patients have non small cell lung cancer and rest have small cell lung cancer. Non small cell lung cancer (NSCLC) has been further classified as per histology into a number of different types, including inter alia adenocarcinoma, squamous cell carcinoma and large cell carcinoma adenocarcinoma are often found in an outer area of the lung. Squamous cell carcinomas are usually found in the center of the lung next to an air tube (bronchus). Large cell carcinomas can occur in any part of the lung. They tend to grow and spread faster than the other two types.

Immunohistochemistry (IHC) refers to the process of detecting molecules in cells of a tissue section by exploiting the principle of antibodies binding specifically to molecules in biological tissues. Immunohistochemical staining is widely used in the diagnosis of abnormal cells such as those found in cancerous tumors.

IHC is also widely used in basic research to understand the distribution and localization of biomarkers and differentially expressed proteins in different parts of a biological tissue.

Desmocollin-3 is expressed in squamous variety of NSCLC and its presence, as detected for example by IHC, is typically used to differentiate squamous cell carcinoma from Adenocarcinoma. Thyroid transcription factor 1 (TTF-1) is expressed in Adenocarcinoma of the Lung and its presence, as detected for example by IHC, is typically used to differentiate Adenocarcinoma from Squamous cell carcinoma. The basis of Immunohistochemistry is to detect presence of expression of a particular biomarker. Desmocollin-3 and TTF-1 are such biomarkers which are specific for Squamous cell carcinoma and Adenocarcinoma of the Lung respectively. TTF-1 is a protein that regulates the transcription of genes. Desmocollin-3 belongs to the Cadherin group of cell adhesion molecules. Desmocollins are calcium dependent adhesion molecules. Desmocollin 1, 2 and 3, are desmosomal component typically found in pseudostratified and stratified epithelia. Desmocollin-3 is expressed on basal most layers of stratified epithelia and its expression decreases gradually in the suprabasal layers. The expression of RNA specific to desmocollin gene is associated with the expression of desmocollins. It has been observed that cells containing a specific desmocollin subtype tend to cluster together to the exclusion of other types.

Historically, first-line treatment for patients with advanced NSCLC has been platinum-based doublet chemotherapy in combination with a third-generation cytotoxic compound such as gemcitabine (Gemzar; Eli Lilly and Company, Indianapolis, Ind.), Paclitaxel (Taxol; Bristol-Myers Squibb, Princeton, N.J.) or Docetaxel (Taxotere; Sanofi-Aventis, Bridgewater, N.J.). Clinical trials of a platinum based therapy in combination with any of these agents demonstrated comparable efficacy, and meta-analyses showed that these regimens offered superior survival and symptom palliation versus best supportive care. The study conducted by Eastern Cooperative Oncology Group (ECOG) comparing four platin-based, two-drug chemotherapy regimens in more than 1100 patients suggests no significant differences in overall survival among the groups.

The first line therapy is offered irrespective of histology of the tumor. The efforts are made to improve the out come of first line therapy without any success.

Recently Bevacizumab is approved as add on therapy to first line therapy for non squamous cell lung cancer. Bevacizumab has been demonstrated in combination with first line therapy to improve outcomes over those seen with first line therapy alone in the treatment of advanced non squamous NSCLC. The two large, phase III, randomized trials leading to these relevant results have administered bevacizumab with carboplatin plus paclitaxel and cisplatin plus gemcitabine as first line therapy Similarly it is also observed that pemetrexed is useful in non squamous carcinoma of lung. Non squamous patients treated with pemetrexed-based therapy experienced longer survival than the comparators (HR, 0.78 and 0.84 respectively), whereas squamous patients had shorter survival (HR, 1.56 and 1.23 respectively). It is recommended that it should not be used in squamous cell carcinoma of lung as it worsens the prognosis.

Thus, histology of tumor plays significant role in improvement with first line therapy by addition of a new drug. IHC helps in defining characteristics of cell types and also deciding histology subtype of a tumor as it helps in choosing appropriate therapy.

There is a significant improvement in outcome of non squamous lung cancer recently but no further improvement is seen in patients suffering from squamous cell carcinoma.

Immune surveillance of body is responsible for eliminating cancer cells before they manifest as tumor. Tumor growth is associated with escape from immune surveillance due to immune suppression by tumor or other causes. Immunosuppression is known to be proportional to size of a tumor. Immunotherapy helps in reconstituting immunity.

Immunotherapy may result in a robust reconstitution of immunity which is able to overcome existing immuno-suppression under such circumstances tumor is eliminated. Initially this will manifest as regression of a tumor. This is typically observed when tumor burden is small. In case immune response generated is not adequate to overcome immuno-suppression but achieves equilibrium with immuno-suppression, tumor doesn't grow in size but remains stationary. There is improvement in survival in absence of tumor response.

Immunotherapy may be used alone or in combination of other cancer therapies for cancer.

DETAIL DESCRIPTION OF FIGURE

Figure 1A:
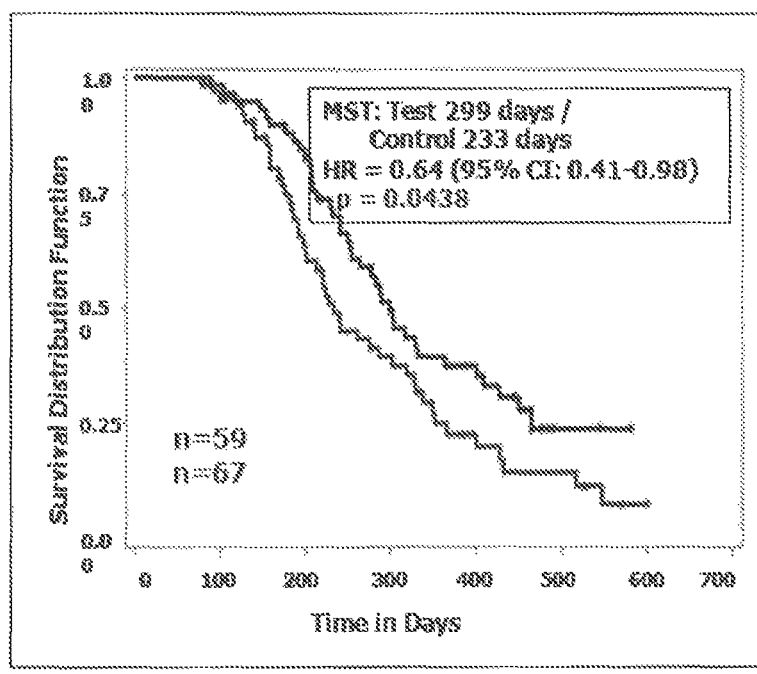
FIG. 1A and FIG. 1B show survival in all patient(s) with non small cell lung cancer.

In all the figures the test arm is having better survival compared to central arm. The test arm is having higher value as survival at end of study period compared to control arm.

OBJECT OF THE INVENTION

An object of present invention is to provide a therapy for desmocollin-3 expressing cancers.

Another object of present invention is to provide a therapy for squamous type of non small cell lung cancer, which is a desmocollin-3 expressing cancer.

Another object of present invention is to provide a therapy for non small cell lung cancer, particularly the squamous type.

Yet another object of present invention is to improve survival of patients suffering from desmocollin-3 expressing cancers.

Yet another object of present invention is to provide a therapy for patients suffering from desmocollin 3 expressing cancers using *Mycobacterium* w.

Yet another object of present invention is to provide a therapy for patients suffering from desmocollin-3 expressing cancers using *Mycobacterium* w along with other cancer therapies.

Yet another object of present invention is to improve survival of patients suffering from desmocollin-3 expressing cancers using *Mycobacterium* w along with conventional therapy.

DETAILED DESCRIPTION OF THE INVENTION

Surprisingly it is observed that immune cells generated following administration of *Mycobacterium* w (Mw) to a mammal express desmocollin-3 (see Example 2). Thus, it appears that Mw causes the appearance of desmocollin-3 expressing immune cells, which may be by causing the generation of new immune cells, or by causing existing immune cells to express desmocollin-3. The immune cells are Peripheral blood mononuclear cells (PBMCs). Desmocollin-3 is responsible for anchoring of activated immune cells on cells/tissues/tumors.

Surprisingly it is observed that therapy using pharmaceutical compositions containing *Mycobacterium* w when administered to patients suffering from desmocollin-3 expressing cancers results in significant advantage in tumor control and survival. Therapy using pharmaceutical compositions containing *Mycobacterium* w administered to patients suffering from non small cell carcinoma was particularly effective; a clinically and statistically significant benefit is seen in patients suffering from squamous cell carcinoma which are known to express desmocollin-3.

The present invention provides *Mycobacterium* w for use in treating desmocollin-3 expressing cancers, preferably squamous cell carcinoma, which is a histological variety of non small cell lung cancer. In particular, the invention is concerned with improving the survival of patients having desmocollin-3 expressing carcinoma.

In another embodiment, the invention provides *Mycobacterium* w for use in treating NSCLC, preferably squamous cell carcinoma.

The inventors through extensive experimentation have found that administration of *Mycobacterium* w improves median survival as well as overall survival of such patients. The median overall survival is preferably improved by at least 10, 20, 30, 40, 50, 60, 70, 80, 90, 100 or 110 days, e.g. by about 70-110 or 90-110 days. The median overall survival is preferably improved by a factor of at least 1.1, 1.2, 1.3, 1.4 or 1.5, most preferably about 1.5.

The median overall survival is preferably at least 240, 250, 260, 270, 280, 290, 300, 310, 320, 330, 30, 350 or 360 days, e.g. 290-365 or 300-360 days from the start of the treatment.

The patient may have any kind of tumor expressing desmocollin-3. The tumor can be of any stage. The tumor may be surgically amenable or surgically non amenable.

The patient may have any stage of Non-Small Cell Lung Cancer, preferably of the squamous carcinoma type, but preferably the patient has an advanced stage of the cancer, such as stage IIIB or IV. Preferably, the patient has an ECOG (Eastern Cooperative Oncology Group) performance status of 0 or 1. The patient is preferably human.

The inventors have found that cells of human embryonic lung carcinoma, human skin malignant melanoma, hepatic carcinoma and several cell types of human pancreatic adenocarcinoma are desmocollin-3 positive. The therapy of the invention is preferably directed to one or more of these cancer types. The inventors have also found that some patients with bladder cancer have bladder cancer cells that are desmocollin-3 positive. Thus, patients that have bladder cancer cells that are desmocollin-3 positive may benefit from treatment with Mw according to the present invention.

The invention therefore provides a novel approach to treating cancer. Cancers or samples thereof may be screened in vivo or in vitro to assess desmocollin-3 expression, for example by immunohistochemistry, RNA analysis and the like. The results of the analysis may be used to determine what treatment the subject should receive. In particular, based on the detection of desmocollin-3 expression, a determination may be made that the subject should be treated with Mw. Thus, there is provided a method of determining what treatment a cancer patient should receive, said method comprising (a) testing whether the cancer of said patient expresses desmocollin-3; and (b) if said cancer expresses desmocollin-3, determining that said patient should be treated with Mw. Alternatively viewed, there is provided a method of diagnosing that a cancer patient is in need to treatment with Mw, said method comprising (a) testing whether the cancer of said patient expresses desmocollin-3; and (b) if said cancer expresses desmocollin-3, determining that said patient should be treated with Mw. Any of said methods may also comprise (c) treating said patient with Mw.

Thus, Mw is preferably used to treat a patient whose cancer has been determined to express desmocollin-3. Thus, cells of the cancer of said patient have preferably been analysed to determine that they express desmocollin-3.

In the therapy according to the invention, *Mycobacterium* w may be used alone or in combination with one or more active agents such as chemotherapeutic agents. The therapeutic agent used in combination with *Mycobacterium* w is selected by a skilled person in the art as per the requirement based on type of cancer, stage of cancer etc. Preferably, the chemotherapeutic agent is selected from Paclitaxel and/or Cisplatin.

In accordance with present invention, also provided is a pharmaceutical composition comprising *Mycobacterium* w and a pharmaceutically acceptable excipient or diluent. The pharmaceutical composition may also comprise a chemotherapeutic agent, which is preferably selected from Paclitaxel and/or Cisplatin.

*Mycobacterium* w is preferably used in killed form, e.g. heat killed. The pharmaceutical composition is preferably formulated to provide a dose of more than $10^6$ cells of *Mycobacterium* w per dose. The *Mycobacterium* w is preferably administered in a dosage of at least $0.5\times10^6$, at least $0.5\times10^7$, or $0.5\times10^8$, or ranging from $0.5\times10^6$ to $0.5\times10^{11}$, more preferably $0.5\times10^8$ to $0.5\times10^{10}$ most preferably about $0.5\times10^9$. *Mycobacterium* w may be administered by any convenient route known, e.g. intravenously (IV) or intradermally.(ID) The dosage schedule may for example involve administration twice or once a week, once every two weeks, once a month, or twice in a 21 day cycle. If used in combination with other agents the time of administration of *Mycobacterium* w in relation to other therapeutic agents/modalities is decided by person skilled in the art, *Mycobacterium* w is preferably administered at least 1 week prior to the first cycle and every 2nd and 3rd week of each cycle when paclitaxel and/or cisplatin is used.

The cycle for other therapeutic agents/modalities, its duration, frequency, interval between two administrations of therapeutic agent/modalities is decided by the person skilled in the art based on requirement. The cycle is preferably of about 21 days for most of the chemotherapeutic agents including paclitaxel and/or cisplatin. The total numbers of cycles for chemotherapy are 4 or more. The numbers of cycles are decided person skilled in the art based on response to therapy, side effects and tolerance to therapy etc. For chemotherapy using paclitxel and/or cisplatin as first line therapy in non small call lung cancer preferably a total of about 4 cycles is used.

Following examples demonstrate the present invention without limiting the scope of the invention:

Example 1

Pharmaceutical Composition as Per Present Invention

Each dose of 0.1 ml contains:

| | |
|---|---|
| *Mycobacterium w* (heat killed) | $0.50 \times 10^9$ |
| Sodium Chloride I.P. | 0.90% w/v |
| Thiomerosal I.P. | 0.01% w/v (As a Preservative) |
| Water for Injection I.P. | q.s to 0.1 ml |

Example 2

The healthy human were randomized to receive *Mycobacterium* w 0.1 ml and PBS (Control) intradermally. After 7 day blood was withdrawn and PBMCs were isolated. The total RNA was extracted from the isolated. The total RNA was used to generate microarray data against Global Human microarray. The data was interpreted as fold change over control. The data shows that desmocollins-3 gene is over expressed by four fold. There is no effect on other desmocollins. There is also no effect on TTF-1 gene.

Example 3

Cancer Cells Expressing Desmocollin-3

The following is a list of cell lines which were evaluated for desmocollin-3 (Table 1)

TABLE 1

| Sr. No. | Cells | Type | Immuno-fluorescence |
|---|---|---|---|
| | | PANCREATIC CANCER | |
| 1 | Panc-1 | Human Pancreatic Adenocarcinoma | Positive |
| 2 | AsPc-1 | Human Pancreatic Adenocarcinoma | Positive |
| 3 | Sw 1990 | Human Pancreatic Adenocarcinoma | Positive |
| 4 | Mia-PaCa2 | Human Pancreatic Adenocarcinoma | Negative |
| | | LUNG CANCER | |
| 5 | L-132 | Human Embryonic lung carcinoma | Positive |
| 6 | A549 | Human alveolar Adenocarcinoma | Negative |
| | | SKIN CANCER | |
| 7 | A375 | Human skin malignant melanoma | Positive |
| | | COLON CANCER | |
| 8 | HT-29 | Human colorectal adenocarcinoma | Negative |
| | | LIVER CANCER | |
| 9 | Hep 3B | Hepatic Carcinoma | Positive |

Example 4

Desmocollin-3 Expressions by Immunohistochemistry

Sections of tumors removed during surgery were stained for presence of or absence of desmocollin-3. The thin paraffin sections of tumors were stained using standard protocol for Immuno histochemistry using antibodies specific for DSC 3. The brief staining procedure includes washing with PBS. Followed by staining with 1:1000 diluted primary antibody (Anti DSC-3 goat polyclonal) for overnight and staining with secondary antibody (Goat anti-mouse IgG-FITC) for 30 minutes.

The findings are in a table. It is seen that none of breast cancers, Head & Neck Cancer, Colon cancer samples expressed desmocollin-3 while one of the three from a recurrent bladder cancer.

TABLE 2

| Sr No | Type of cancer | No of samples | No of samples positive | No of samples negative |
|---|---|---|---|---|
| 1 | Head and neck | 7 | 0 | 7 |
| 2 | Bladder | 3 | 1 | 2 |
| 3 | Colon | 8 | 0 | 8 |
| 4 | Breast | 7 | 0 | 7 |

Example 5

Efficacy of Pharmaceutical Composition in Squamous Cell Lung Cancer

In an open label, multicentric, randomized, comparative controlled clinical trial, *Mycobacterium* w was evaluated in combination with Paclitaxel and Cisplatin for its effect on improvement in overall survival in patients with advanced non small cell lung cancer.

TABLE 3

| Agent | Dose | Route | Schedule |
|---|---|---|---|
| Paclitaxel | 175 mg/m² | IV over 3 hrs before Cisplatin | Day 1 of each cycle |

TABLE 3-continued

| Agent | Dose | Route | Schedule |
|---|---|---|---|
| Cisplatin | 100 mg/m$^2$ | IV over a hr after completion of Paciltaxel through separate IV line | Day 1 of each cycle |
| Mycobacterium w | 0.1 ml* | Intradermal 0.1 ml over each deltoid on first visit & 0.1 ml subsequently | At least 1 week prior to first cycle & every 2$^{nd}$ & 3$^{rd}$ wek of all the cycles |

*Containing 0.50 × 10$^9$ heat killed Mycobacterium w.

The study was conducted on total 221 patients.

Dosage Schedule:

Test arm received Paclitaxel+Cisplatin by intravenous infusion on day 1 of a 21 days cycle for a total of 4 cycles. In addition, Mycobacterium w was given intradermally at least one week prior to the first cycle of chemotherapy and then in every second and third week of all the cycles of chemotherapy.

Control arm received only chemotherapy (Paclitaxel+Cisplatin) by intravenous infusion on a 21 days cycle×4 cycles.

The Patients Enrolled in the Trial Met Following Inclusion Criteria:

Histologically or cytologically confirmed Non-Small Cell Lung Cancer, Stage IIIB or IV.

Age: 18 years and above

ECOG status in 0-1 range

Absolute neutrophil count≥1500/mm$^3$, Platelet count≥1,00,000/mm$^3$

Hemoglobin≥9.0 g/dL

AST and ALT≤2.5 times Upper Limit of Normal (ULN) (5 times ULN if liver metastasis present)

Bilirubin not greater than 1.5 times ULN (3 times ULN if liver involvement).

Creatinine≤upper limit of normal (ULN)

Negative pregnancy test for women of child bearing potential prior to entry into the trial Ability to understand and the willingness to sign a written informed consent document Following Patients were Excluded:

Patient who had received cytotoxic chemotherapy or radiotherapy prior to entering the study Patient with systematic brain metastasis History of allergic reaction attributed to Paclitaxel, Cisplatin or Mycobacterium w or any of their ingredients Pregnant women or nursing women Uncontrolled intercurrent illness that would limit compliance with study requirements HIV positive patients Previous splenectomy Efficacy Analysis:

a. All the analysis reported is as per protocol. Survival was defined as the time from randomization to death from any cause, and progression free survival as the time from randomization to documented disease progression or death.

Results:

b. A total of 221 patients were enrolled in the trial, of which 109 were allocated to the test arm and 112 to the control arm. Both the groups were comparable in all baseline characteristics (Table-4).

TABLE 4

| Baseline Characteristics | | |
|---|---|---|
| Parameters | Test N = 109 | Control N = 112 |
| Sex [No. (%)] | | |
| Female | 18 (16.6%) | 14 (12.5%) |
| Male | 91 (83.4%) | 98 (87.5%) |
| Age (yrs) | 56.4 ± 11.0 | 56.9 ± 10.4 |
| Weight (Kg) | 49.8 ± 10.7 | 50.5 ± 8.9 |
| ECOG I | 63 (57.8%) | 66 (58.9%) |
| ECOG 0 | 46 (42.2%) | 46 (41.1%) |
| Stage of Disease IIIB | 54 (49.54%) | 61 (54.46%) |
| Stage of Disease IV | 55 (50.46%) | 51 (45.54%) |
| NSCLC Type | | |
| Adenocarcinoma | 45 | 50 |
| Squamous Cell Carcinoma | 19 | 24 |
| Others | 42 | 34 |
| Large Cell Carcinoma | 3 | 4 |

Figure 1B:
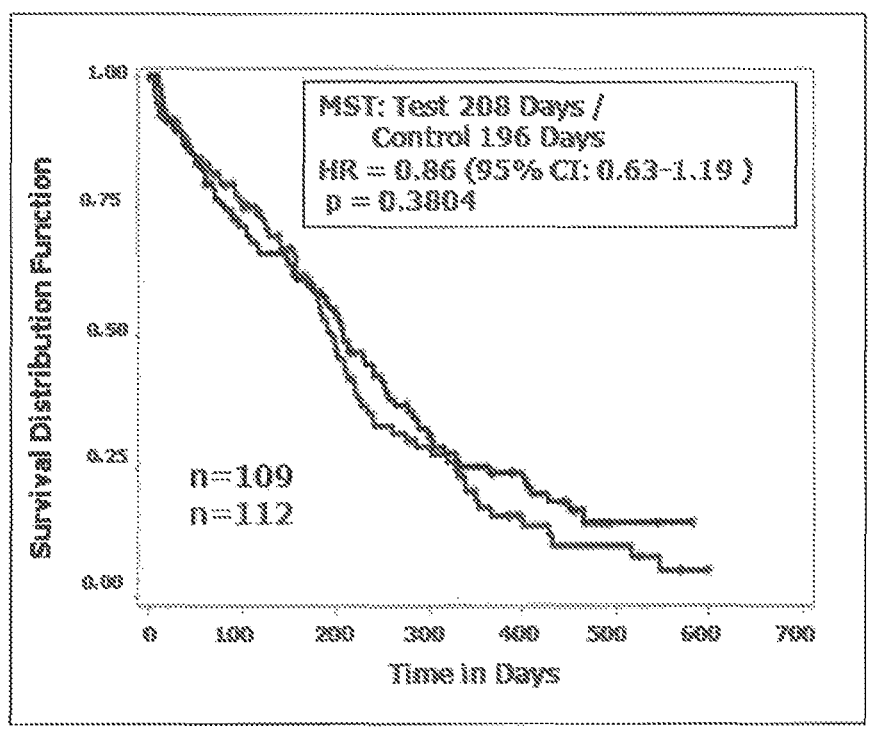

Use of Mycobacterium w is associated with significant improvement in overall survival (FIG. 1) in test arm in comparison to the control arm. Median over all survival was 233 days in control arm and was improved by 66 days to 299 days in test arm in subjects who completed all four cycles of chemotherapy as planned (HR=0.64; 95% CI: 0.41-0.98; p=0.0438). As per intent to treat analysis it was 196 days in control arm and improved by 12 days to 208 days in test arm (HR=0.86; 95% CI: 0.63-1.19; p=0.380). This was clinically not relevant and statistically not significant.

Figure 2A:
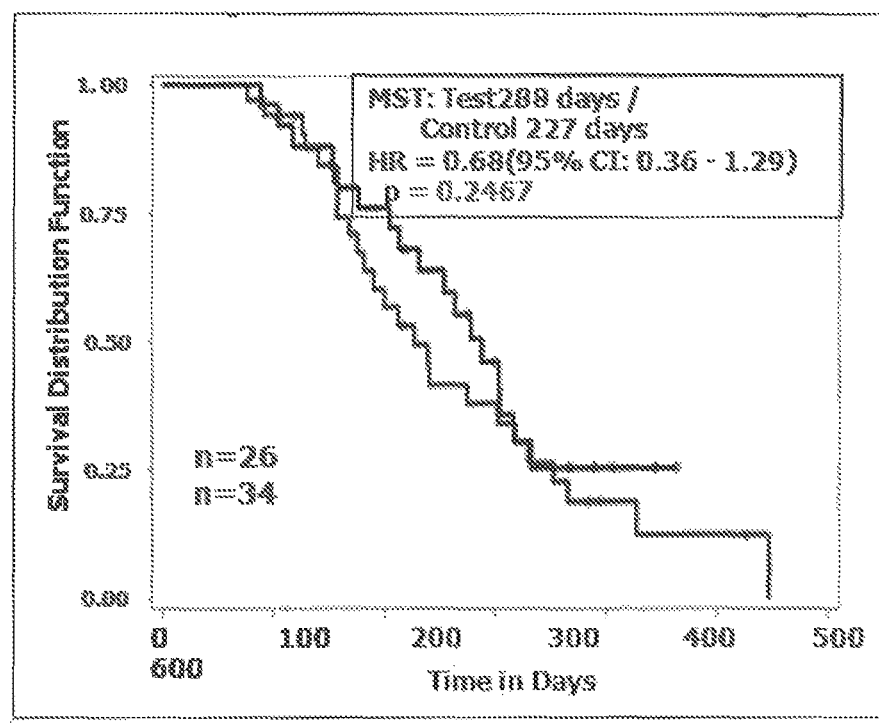
FIG. 2A and FIG. 2B show survival in all patient(s) with adenocarcinoma.
Figure 2B:
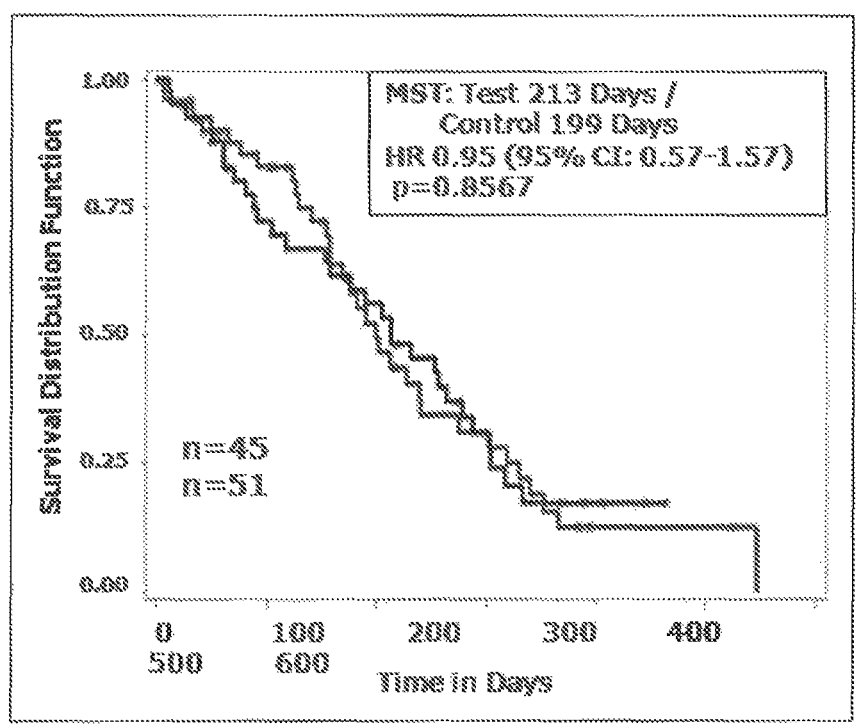
Figure 3A:
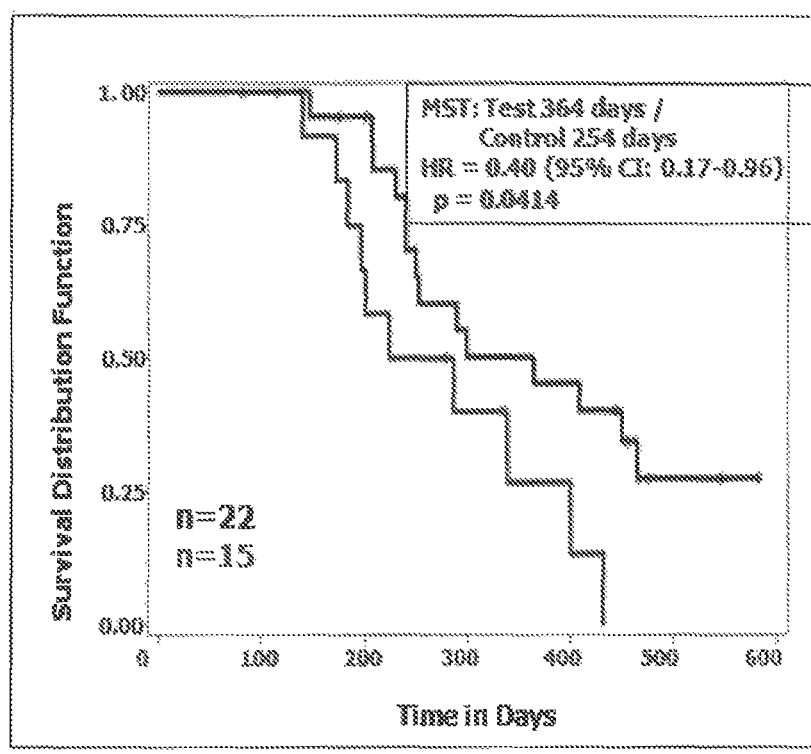
FIG. 3A and FIG. 3B show survival in all patient(s) with squamous cell carcinoma of lung.
Figure 3B:
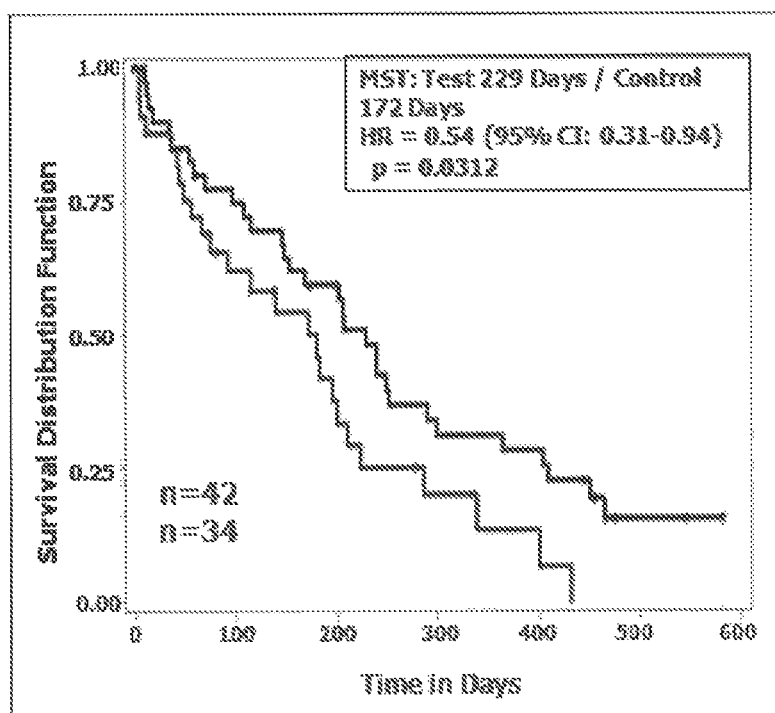

Improvement in survival is more in patients with Squamous cell carcinoma (FIG. 2) in comparison to those with Adenocarcinoma (FIG. 3), with median survival 364 days and 288 days, respectively in those who completed four cycles of chemotherapy. The difference in median survival in relation to control group was 110, and 61 days, respectively. The difference in survival for those patients who completed four cycles of chemotherapy was statistically significant for squamous cell carcinoma (HR=0.40; 95% CI: 0.17-0.96; p=0.0414) but was not statistically significant for adenocarcinoma (HR=0.68; 95% CI: 0.36-1.29; p=0.2467).

Similar findings are seen in intent to treat (ITT) analysis. Improvement in survival appears to be more in patients with Squamous cell carcinoma in comparison to those with Adenocarcinoma, with median survival 229 days and 213 days, respectively. The difference in median survival in relation to control group was 57, and 14 days respectively. The difference in survival for patients with squamous cell carcinoma was statistically significant (HR=0.54; 95% CI: 0.31-0.94: p=0.0312) but was not statistically significant for adenocarcinoma (HR=0.95; 95% CI: 0.57-1.57; p=0.8567).

Thus clinically relevant and statistically significant improvement in survival is seen with squamous cell carcinoma and not in adenocarcinoma by intent to treat analysis as well as analysis for patients who completed four cycles of chemotherapy as planned.

Example 6

Efficacy of Mw in Desmocollin-3 Expression Tumor

In 11 patients with BCG refractory bladder cancer was performed TUR (Transurethral resection). Following 0.1 ml Mw was administered intradermally every two weeks for six administrations and every 4 weeks for six administrations and every 8 week for three administrations. Patients achieved remissions lasting for more than 15 months were having tumors which were desmocollin-3 positive. Others having recurrence of a tumor in less than three months had desmocollin-3 negative tumors.

We claim:

1. A method of treating a subject suffering from a desmocollin 3 expressing cancer comprising administering to said subject a therapeutically effective amount of inactivated *Mycobacterium* w.

2. The method of claim 1, wherein said desmocollin 3 expressing cancer is a squamous type of non small cell lung cancer.

3. The method of claim 1, wherein the desmocollin-3 expressing cancer is selected from the group consisting of human embryonic lung carcinoma, malignant melanoma, hepatic carcinoma, pancreatic cancer and bladder cancer or a combination thereof.

4. The method of claim 1, wherein said *Mycobacterium* w increases the survival of the subject suffering from the desmocollin-3 expressing cancer.

5. The method of claim 1, wherein said *Mycobacterium* w is used in a dosage of more than 106 cells per dose.

6. The method of claim 1, wherein said *Mycobacterium* w is used in combination with at least one other therapeutic agent or modalities.

7. The method of claim 6, wherein said at least one other therapeutic agent or modalities is a chemotherapeutic agent.

* * * * *